United States Patent
Gysling

(10) Patent No.: US 7,059,172 B2
(45) Date of Patent: *Jun. 13, 2006

(54) PHASE FLOW MEASUREMENT IN PIPES USING A DENSITY METER

(75) Inventor: Daniel L. Gysling, Glastonbury, CT (US)

(73) Assignee: Weatherford/Lamb, Inc., Houston, TX (US)

( * ) Notice: Subject to any disclaimer, the term of this patent is extended or adjusted under 35 U.S.C. 154(b) by 115 days.

This patent is subject to a terminal disclaimer.

(21) Appl. No.: 10/342,052

(22) Filed: Jan. 14, 2003

(65) Prior Publication Data

US 2003/0136186 A1    Jul. 24, 2003

Related U.S. Application Data

(63) Continuation-in-part of application No. 10/186,382, filed on Jun. 28, 2002, now Pat. No. 6,698,297, and a continuation-in-part of application No. 10/010,183, filed on Nov. 7, 2001, now Pat. No. 6,971,259.

(51) Int. Cl.
*G01N 9/00* (2006.01)
*G01N 29/00* (2006.01)
*G01N 33/00* (2006.01)

(52) U.S. Cl. .................... 73/32 A; 73/61.41; 73/61.49; 73/61.79

(58) Field of Classification Search ................ 73/32 A, 73/32 R, 24.01, 24.05, 24.06, 61.79, 61.41, 73/61.47, 61.49, 597, 653–657, 579, 861.04, 73/861.05, 861.18

See application file for complete search history.

(56) References Cited

U.S. PATENT DOCUMENTS 3,149,492 A    9/1964    Weinberg (Continued)

FOREIGN PATENT DOCUMENTS

DE    19511234    12/1995

(Continued)

OTHER PUBLICATIONS

U.S. Appl. No. 09/346,607, filed Jul. 2, 2000, Gysling et al.

(Continued)

*Primary Examiner*—Helen Kwok
(74) *Attorney, Agent, or Firm*—Patterson & Sheridan, LLP.

(57) ABSTRACT

The present invention discloses an apparatus for determining the density and the phase fraction of a fluid flowing in a conduit. The apparatus comprises a fiber optic density meter situated along the conduit that provides a signal indicative of the density of the fluid. The density meter includes two sound speed meters disposed at different sensing regions along the pipe. The sensing regions have a substantially different cross sectional area compliance. Each sound speed meter measures an acoustic pressure within the pipe at its corresponding axial location and provides a signal indicative of the effective fluid sound speed at its corresponding sensing region. Because each sensing region has a substantially different cross sectional area compliance, the density of the fluid is determined by the difference between the effective fluid sound speed signals. From the effective sound speed at either sensing region or from a separate acoustic sensor array, the infinite fluid sound speed may be determined. The phase fraction of the fluid can then be calculated by combining the infinite fluid sound speed, the fluid density, and known individual component densities and component sound speeds (oil, water, and/or gas).

41 Claims, 6 Drawing Sheets

U.S. PATENT DOCUMENTS

| | | |
|---|---|---|
| 3,851,521 A | 12/1974 | Ottenstein |
| 4,080,837 A | 3/1978 | Alexander |
| 4,114,439 A | 9/1978 | Fick |
| 4,144,768 A | 3/1979 | Andersson |
| 4,159,646 A | 7/1979 | Paulsen |
| 4,164,865 A | 8/1979 | Hall |
| 4,236,406 A | 12/1980 | Reed |
| 4,275,602 A | 6/1981 | Fujishiro |
| 4,445,389 A | 5/1984 | Potzick |
| 4,499,418 A | 2/1985 | Helms |
| 4,515,473 A | 5/1985 | Mermelstein |
| 4,520,320 A | 5/1985 | Potzick |
| 4,546,649 A | 10/1985 | Kantor |
| 4,706,501 A | 11/1987 | Atkinson |
| 4,788,852 A | 12/1988 | Martin |
| 4,813,270 A | 3/1989 | Baillie |
| 4,862,750 A | 9/1989 | Nice |
| 4,864,868 A | 9/1989 | Khalifa |
| 4,884,457 A | 12/1989 | Hatton |
| 4,896,540 A | 1/1990 | Shakkottai |
| 4,932,262 A | 6/1990 | Wlodarczyk |
| 4,947,127 A | 8/1990 | Helms |
| 4,950,883 A | 8/1990 | Glenn |
| 4,976,151 A | 12/1990 | Morishita |
| 4,996,419 A | 2/1991 | Morey |
| 5,024,099 A | 6/1991 | Lee |
| 5,031,460 A | 7/1991 | Kanenobu |
| 5,040,415 A | 8/1991 | Barkhoudarian |
| 5,051,922 A | 9/1991 | Toral |
| 5,058,437 A | 10/1991 | Chaumont |
| 5,083,452 A | 1/1992 | Hope |
| 5,099,697 A | 3/1992 | Agar |
| 5,115,670 A | 5/1992 | Shen |
| 5,152,181 A | 10/1992 | Lew |
| 5,207,107 A | 5/1993 | Wolf |
| 5,218,197 A | 6/1993 | Carroll |
| 5,317,576 A | 5/1994 | Leonberger |
| 5,321,991 A | 6/1994 | Kalotay |
| 5,347,873 A | 9/1994 | Vander Heyden |
| 5,359,897 A | 11/1994 | Hamstead et al. ............ 73/597 |
| 5,361,130 A | 11/1994 | Kersey |
| 5,363,342 A | 11/1994 | Layton |
| 5,367,911 A | 11/1994 | Jewell |
| 5,372,046 A | 12/1994 | Kleven |
| 5,398,542 A | 3/1995 | Vasbinder |
| 5,401,956 A | 3/1995 | Dunphy |
| 5,426,297 A | 6/1995 | Dunphy |
| 5,440,932 A | 8/1995 | Wareham |
| 5,493,390 A | 2/1996 | Varasi |
| 5,493,512 A | 2/1996 | Peube |
| 5,513,913 A | 5/1996 | Ball |
| 5,546,813 A | 8/1996 | Hastings et al. ......... 73/861.29 |
| 5,548,530 A | 8/1996 | Baumoel .................... 364/509 |
| 5,564,832 A | 10/1996 | Ball |
| 5,576,497 A | 11/1996 | Vignos |
| 5,591,922 A | 1/1997 | Segeral |
| 5,597,961 A | 1/1997 | Marrelli |
| 5,639,667 A | 6/1997 | Heslot |
| 5,642,098 A | 6/1997 | Santa Maria |
| 5,644,093 A | 7/1997 | Wright |
| 5,654,551 A | 8/1997 | Watt |
| 5,670,720 A | 9/1997 | Clark |
| 5,680,489 A | 10/1997 | Kersey |
| 5,689,540 A | 11/1997 | Stephenson |
| 5,708,211 A | 1/1998 | Jepson |
| 5,719,329 A | 2/1998 | Jepson et al. ............... 73/61.49 |
| 5,730,219 A | 3/1998 | Tubel |
| 5,732,776 A | 3/1998 | Tubel |
| 5,741,980 A | 4/1998 | Hill |
| 5,803,167 A | 9/1998 | Bussear |
| 5,804,713 A | 9/1998 | Kluth |
| 5,835,884 A | 11/1998 | Brown ........................ 702/45 |
| 5,842,347 A | 12/1998 | Kinder |
| 5,845,033 A | 12/1998 | Berthold |
| 5,906,238 A | 5/1999 | Carmody |
| 5,907,104 A | 5/1999 | Cage |
| 5,908,990 A | 6/1999 | Cummings |
| 5,925,821 A | 7/1999 | Bousquet |
| 5,925,879 A | 7/1999 | Hay |
| 5,939,643 A | 8/1999 | Oertel |
| 5,956,132 A | 9/1999 | Donzier |
| 5,959,547 A | 9/1999 | Tubel |
| 5,963,880 A | 10/1999 | Smith |
| 5,975,204 A | 11/1999 | Tubel |
| 5,992,519 A | 11/1999 | Ramakrishnan |
| 5,996,690 A | 12/1999 | Shaw |
| 6,002,985 A | 12/1999 | Stephenson |
| 6,003,383 A | 12/1999 | Zielinska |
| 6,003,385 A | 12/1999 | De Vanssay |
| 6,009,216 A | 12/1999 | Pruett |
| 6,016,702 A | 1/2000 | Maron |
| 6,158,288 A | 12/2000 | Smith |
| 6,202,494 B1 | 3/2001 | Riebel et al. ............ 73/861.29 |
| 6,216,532 B1 | 4/2001 | Stephenson |
| 6,233,374 B1 | 5/2001 | Ogle |
| 6,279,660 B1 | 8/2001 | Hay |
| 6,349,599 B1 | 2/2002 | Lynnworth et al. ........... 73/644 |
| 6,354,147 B1 * | 3/2002 | Gysling et al. ............ 73/61.79 |
| 6,371,982 B1 | 4/2002 | Berg et al. .................... 623/1.4 |
| 6,442,996 B1 | 9/2002 | Thurston et al. ........... 73/24.01 |
| 6,446,494 B1 | 9/2002 | Hastings et al. ........... 73/54.41 |
| 6,450,037 B1 | 9/2002 | McGuinn et al. .............. 73/705 |
| 6,502,465 B1 * | 1/2003 | Vedapuri et al. ......... 73/861.04 |
| 6,601,458 B1 * | 8/2003 | Gysling et al. .......... 73/861.04 |

FOREIGN PATENT DOCUMENTS

| | | |
|---|---|---|
| EP | 0684458 | 5/1995 |
| FR | 2 357 868 | 7/1976 |
| JP | 406082281 | 9/1992 |
| WO | WO 93/14382 | 7/1993 |
| WO | WO 96/04528 | 2/1996 |
| WO | WO 00 00793 | 1/2000 |
| WO | WO 00/00799 | 1/2000 |
| WO | WO 01/01088 A1 | 1/2001 |

OTHER PUBLICATIONS

U.S. Appl. No. 09/345,827, filed Jul. 2, 1999, Gysling et al.
U.S. Appl. No. 09/346,606, filed Jul. 2, 1999, Gysling et al.
U.S. Appl. No. 09/346,604, filed Jul. 2, 1999, Gysling et al.
U.S. Appl. No. 09/346,605, filed Jul. 2, 1999, Gysling et al.
U.S. Appl. No. 09/519,785, filed Mar. 7, 2000, Gysling et al.
U.S. Appl. No. 09/740,760, filed Nov. 29, 2000, Davis et al.
U.S. Appl. No. 09/344,069, filed Jun. 25, 1999, Gysling.
Mesch. F. (1990) "Speed and Flow Measurement by an Intelligent Correlation System", Advances in Instrumentation and Control, Research Triangle Park, NC, part 4, p. 1899-1914.
Gysling, D. (1999) "Development of a Fiber Optic Downhole Multiphase Flow Meter", in "Field Applications & New Technologies for Multiphase Metering", Multiphase Technology Series Conference. Aberdeen, Scotland.
Beranek, I., and Ver. I. (1992) in "Noise and Vibration Control Engineering, Principles and Application", John Wiley & Sons, Inc., Chapter 14, p. 537-541.
Dowling, A. and Williams, J. in "Sound and Sources of Sound", Ellis Horwood Limited. Section 4. p. 79-80, no date.

Kersey, A. et al. (1993) "Multiplexed Fiber Bragg Grating Strain-Sensor System with a Fiber Fabry-Perot Wavelength Filter", Optic Letters, 18:1370-1372.

Dandridge. A. & Cogdell. G. (1991) "Fiber Optic Sensors for Navy Applications", IEEE. LCS. 2:81-89.

Nielsen. R. (1991) "Sonar Signal Processing", Artech Huse Inc., Chapter 2, p.: 51-59.

Krim A. and Viberg M. (1996) "Two Decades of Array Signal Processing Research", IEEE Signal Processing Magazine, p.: 67-94.

Kersey A. and Darkin. J., Editors (1992) SPIE vol. 1586, "Distributed and Multiplexed Fiber Optic Sensors", p.: 1-243.

Nerby et al. "A cost effective technique for production well testing". (1995) Offshore Technology Conference, p.:505-515.

"Noise and Vibration Control Engineering Principles and Applications", Leo L., Beranek and Istvan L. Ver. A Wiley Interscience Publication, pp. 537-541, no date.

"Development of a Fiber Optic Downhole Multiphase Flow Meter", Daniel L. Gysling, 5th Inter. Conference-Multiphase Technology Series, Feb. 1999, Aberdeen, Scotland.

"Sound and Sources of Sound", by A.P. Dowling and J.E. Williams, pp. 224-229, no date.

"Speed and Flow Measurement by an Intelligent Correlation System" by Franz Mesch. Advances in Instrumentation and Control, 45 (1990) Part 4. Research Triangle Park, NC, US.

PCT International Search Report, International Application No. PCT/GB02/05004, dated Feb. 13, 2003.

* cited by examiner

PHASE FLOW MEASUREMENT IN PIPES USING A DENSITY METER

CROSS-REFERENCES TO RELATED APPLICATIONS

This application is a continuation-in-part of U.S. patent application Ser. Nos. 10/010183, entitled "Fluid Density Measurement in Pipes Using Acoustic Pressures," filed Nov. 7, 2001 now U.S. Pat. No. 6,971,259; and 10/186,382, entitled "Venturi Augmented Flow Meter," filed Jun. 28, 2002 now U.S. Pat. No. 6,698,297. Priority is claimed to all of these applications, and both are incorporated herein by reference.

This application contains subject matter related to that disclosed in U.S. Pat. No. 6,354,147, entitled "Fluid Parameter Measurement in Pipes Using Acoustic Pressures," issued Mar. 12, 2002; U.S. patent application Ser. No. 09/344,070, entitled "Measurement of Propagating Acoustic Waves in Compliant Pipes," filed Jun. 25, 1999; U.S. patent application, Ser. No. 09/344,069, entitled "Displacement Based Pressure Sensor Measuring Unsteady Pressure in a Pipe," filed Jun. 25, 1999; and U.S. patent application, Ser. No. 09/344,093, entitled "Non-Intrusive Fiber Optic Pressure Sensor for Measuring Unsteady Pressures within a Pipe," filed Jun. 25, 1999, all of which are incorporated herein by reference.

TECHNICAL FIELD

This invention relates to fluid parameter measurements in pipes, and more particularly to determining the phase fraction of a fluid in a pipe by measuring the fluid sound speed and the fluid density. The measurements exploit the interaction between conduit flexibility, sound speed propagation, and density of the fluid within a conduit.

BACKGROUND ART

It is well known that by measuring the sound speed ($a_{mix}$) of a fluid flowing in a pipe, various parameters of the fluid may be determined, such as is described in U.S. Pat. No. 4,080,837, entitled "Sonic Measurement of Flow Rate and Water Content of Oil-Water Streams," to Alexander et al.; U.S. Pat. No. 5,115,670, entitled "Measurement of Fluid Properties of Two-Phase Fluids Using an Ultrasonic Meter," to Shen; and U.S. Pat. No. 4,114,439, entitled "Apparatus for Ultrasonically Measuring Physical Parameters of Flowing Media," to Fick. Such techniques utilize a pair of acoustic transmitters/receivers (transceivers) to generate a sound signal and to measure the time it takes for the sound signal to travel between the transceivers. This is also known as a "sing-around" or "transit time" method. However, such techniques have a variety of drawbacks such as requiring precise control of the acoustic source, difficulties with inhomogeneous multiphase flows, and costly and/or complex to implement via electronics.

To elaborate, these techniques use ultrasonic acoustic signals as the sound signal measured, which are high frequency, short wavelength signals (i.e., wavelengths that are short compared to the diameter of the pipe). Typical ultrasonic devices operate near 200 k Hz, which corresponds to a wavelength of about 0.3 inches in water. In general, to allow for signal propagation through the fluid in an unimpeded and thus interpretable manner, the fluid should be homogeneous down to scale lengths of several times smaller than the acoustic signal wavelength. Thus, the criterion for homogeneity of the fluid becomes increasingly stricter with shorter wavelength signals. Consequently, inhomogeneities in the fluid, such as bubbles, gas, dirt, sand, slugs, stratification, globules of liquid, and the like, will reflect or scatter the transmitted ultrasonic signal. Such reflection and scattering inhibit the ability of ultrasonic instruments to determine the propagation velocity. For this reason, the application of ultrasonic flow meters has been limited primarily to well mixed flows.

Gamma-densitometers are widely used in the art for performing density measurements of fluids within pipes. These devices utilize a nuclear source to expose the fluids to a gamma radiation beam and measure density based on gamma beam absorption. The primary drawbacks of this type of density meter are the environmental and safety issues associated with the nuclear sources.

Another prior art method of determining the density of a fluid within a pipe is through the use of Coriolis meter. A Coriolis meter measures mass flow and density as the primary measurements by tracking the natural frequency of a vibrating pipe filled with the fluid. These devices require a vibration source, among other elements, which make Coriolis meters mechanically complex and relatively expensive to install and maintain.

As well as determining density, it is often useful in a production environment to determine the phase fraction of components flowing within the pipe. Flow meters for determining phase fractions are known in the art. See, e.g., U.S. Pat. No. 6,354,147, entitled "Fluid Parameter Measurement in Pipes Using Acoustic Pressures," issued Mar. 12, 2002, which is incorporated by reference herein in its entirety. In this patent, a spatial array of pressure sensors, preferably fiber optic sensors, are coupled to the outside of the pipe. These sensors measure the speed that sound waves travel through the fluid by sensing the acoustic perturbations caused by naturally occurring sound waves in the fluid in the pipe. Because of the relationship between the fluid mixture sound speed and the sound speed of the components, the phase fractions of the fluid can be solved for. Moreover, if the density of the fluid can be determined, the phase fractions for a three phase fluid can be directly solved for. As typical pipelines in the oil and gas industry contain more than two phases, i.e. water, gas and oil, measuring the phase fraction of a three phase fluid mixture would be desirable.

Thus, it is desirable to provide an apparatus capable of not only measuring the density of a fluid but also the phase fraction of a multiphase fluid.

SUMMARY OF THE INVENTION

The present invention discloses an apparatus for determining the density and the phase fraction of a fluid flowing in a conduit. The apparatus comprises a fiber optic density meter situated along the conduit that provides a signal indicative of the density of the fluid. The density meter includes two sound speed meters disposed at different sensing regions along the pipe. The sensing regions have substantially different cross sectional area compliances. Each sound speed meter measures a multitude of acoustic pressures from an axial array of transducers at its corresponding axial location and provides a signal indicative of the effective fluid sound speed, $a_{eff}$ at its corresponding sensing region. Because each sensing region has a substantially different cross sectional area compliance, yet essentially identical fluid parameters, the density of the fluid is determined by the difference between the effective fluid sound speed signals.

From the effective sound speed measurement $\alpha_{eff}$ at either sensing region, the infinite fluid sound speed $\alpha_{mix}$ may be determined by numerous spatial array processing techniques such as described in detail in incorporated '147 patent. The phase fraction of the fluid can then be determined by combining the infinite fluid sound speed $\alpha_{mix}$, the fluid density, and known individual component densities and component sound speeds (oil, water, and/or gas) by the method described in detail below.

The foregoing and other objects, features, and advantages of the present invention will become more apparent in light of the following detailed description of exemplary embodiments thereof.

DETAILED DESCRIPTION OF THE INVENTION

Figure 1:
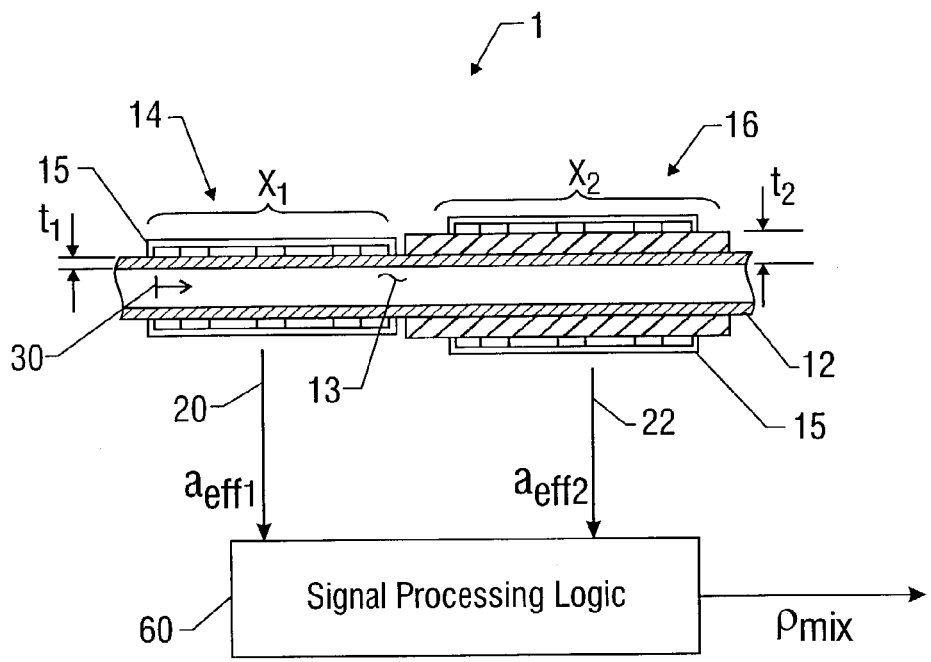
FIG. 1 is a schematic block diagram of a density meter system, in accordance with the present invention.

The density meter 1 of FIG. 1 uses a pair of sound speed meters 14, 16 placed at axial locations, or sensing regions, $X_1$, $X_2$ along the pipe, or conduit, 12 for measuring the density of at least one fluid in a pipe 12. The sound speed meters 14, 16 provide the effective fluid sound speed $\alpha_{eff1}$ and $\alpha_{eff2}$ of the fluid/pipe system on lines 20, 22 which are provided to signal processing logic 60. The logic then determines the density of the fluid (or mixture) in the pipe 12 using the relationships between the compliance of the pipe and various fluid parameters as will be more fully described below. Numerous sensing and processing techniques may be employed to determine the infinite sound speed $\alpha_{mix}$ of the fluid from the measured effective sound speed $\alpha_{eff}$, such as those disclosed in U.S. Pat. No. 6,354,147, entitled "Fluid Parameter Measurement in Pipes Using Acoustic Pressures," issued Mar. 12, 2002, the disclosure of which is incorporated herein by reference in its entirety. By determining the infinite sound speed $\alpha_{mix}$ and incorporating the density of the fluid, the phase fraction of a fluid can be determined.

Some or all of the functions within the logic 60 may be implemented in software (using a microprocessor or computer) and/or firmware, or may be implemented using analog and/or digital hardware, having sufficient memory, interfaces, and capacity to perform the functions described.

The effective fluid sound speeds $\alpha_{eff1}$ and $\alpha_{eff2}$ are provided to logic 60 wherein the logic calculates the density of the fluid from the difference in the effective sound speeds as will be more fully described below. Sound speed meters 14, 16 utilize acoustic pressure signals that, as measured, are lower frequency (and longer wavelength) signals than those used for ultrasonic flow meters of the prior art, as explained in the incorporated '147 patent. Thus, the current invention is more tolerant to inhomogeneities in the flow.

The typical frequency range for acoustic pressure signals of the present invention is from about 10 Hz to about 10,000 Hz. The acoustic pressure signals are generated within the fluid of the pipe 12 by a variety of non-discrete sources such as remote machinery, pumps, valves, elbows, as well as the fluid flow itself. It is this last source, the fluid flowing within the pipe, which is a generic source of acoustic noise that assures a minimum level of acoustics for any fluid piping systems for which the present invention takes unique advantage. The flow generated acoustics increase with mean flow velocity and the overall noise levels (acoustic pressure levels) are a function of the generating mechanism and the damping mechanism. Experience indicates that pipe systems typically have sufficient ambient noise levels of 100 to 180 db (ref to 20 µPa).

No external discrete noise source is required within the present invention and thus may operate using passive listening. It is within the scope of the present invention that the sound speed meter or sensor 14, 16 spacing may be known or arbitrary and that as few as two sensors are required if certain information is known about the acoustic properties of the system as will be more fully described below.

As is known and as is described in the references incorporated herein, planar compression waves 30 propagating within a fluid contained within a pipe 12 exert an unsteady internal pressure loading on the pipe. The degree to which the pipe displaces as a result of the unsteady pressure loading influences the speed of propagation of the compression wave 30 within the fluid/pipe system. For a given fluid, the more compliant the pipe, the greater the reduction of the propagation velocity of the compression wave. Also, for a given pipe stiffness, the denser the fluid and the higher the infinite domain sound speed, i.e., the speed of sound in an unbounded media, the greater the reduction in the propagation velocity due to the pipe flexibility or compliance. More specifically, the relationship between the infinite domain sound speed ($\alpha_{mix}$), density ($\rho_{mix}$) of a fluid, the 16 elastic modulus of the pipe (E), thickness of the pipe (t), the radius of a vacuum-backed 17 cylindrical pipe (R), and the effective propagation velocity ($\alpha_{eff}$) for a one dimensional 18 compression wave is given by the following expression:

$$a_{eff} = \frac{1}{\sqrt{\frac{1}{a_{mix}^2} + \rho_{mix}\frac{2R}{Et}}} \quad \text{(Eq. 1)}$$

Figure 2:
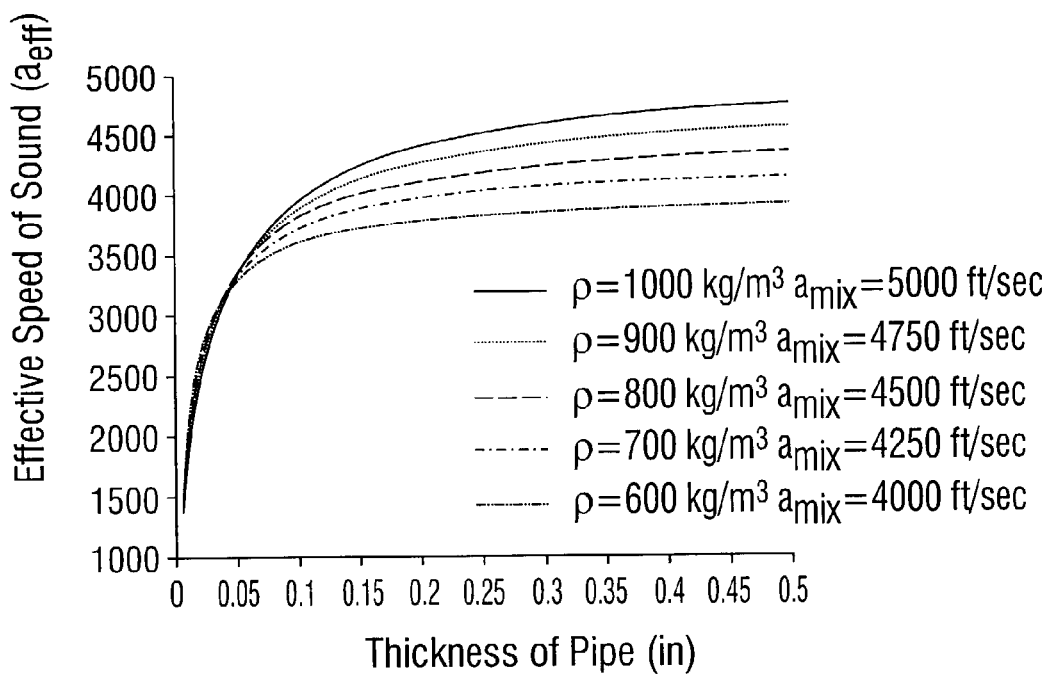
FIG. 2 is a graphical representation of the effective sound speed of a fluid/pipe for various pipe wall thicknesses, in accordance with the present invention.

FIG. 2 shows the effective propagation velocity, or effective sound speed for a specific example of the density meter 1 of FIG. 1 in accordance with the present invention. In this particular embodiment, the effective sound speed is shown for a fluid contained in a vacuum-backed, cylindrical steel pipe with acoustic propagation velocities and density representative of hydrocarbon liquid and water mixtures as typically found in the oil and gas industry. FIG. 2 shows the effect of varying the compliance of the pipe/fluid system by changing the wall thickness of a 5.50 inch OD steel pipe from some theoretical minimum value to a thickness of 0.5 inches for five different fluids having densities from 600 to 1000 kg/m$^3$. As shown in FIG. 2, varying the thickness of the pipe has a significant effect on the effective sound speed of the fluid/pipe system. For simplicity sake, the present invention is described with regard to particular embodiments comprising vacuum-backed conduits having sufficiently low frequencies (compared to breathing mode and resonant frequencies of the pipe) such that the pertinent dynamical response is captured by the static compliance of the pipe. The pipe may be vacuum-backed by a concentric shell 15 (FIG. 1) or other suitable structure to isolate the sensing regions $X_1$, $X_2$ from the outside environment. In alternative embodiments, the sensing regions $X_1$, $X_2$ may be isolated within the concentric shell 15 by a known fluid or air. It is important that a static fluid having lower acoustic impedance than the fluid flowing within the pipe surround the sound speed meters. The advantages and effect of the vacuum backed pipe, as well as other isolation techniques, are described in U.S. patent application Ser. No. 09/344,070, entitled "Measurement of Propagating Acoustic Waves in Compliant Pipes," filed Jun. 25, 1999, which is incorporated herein by reference in its entirety.

Equation 1 can be generalized in terms of the cross-sectional area compliance-($\sigma_{conduit}$) of the pipe, the infinite sound speed, density of the fluid, and the effective sound speed of the pipe/fluid system as given by:

$$\frac{1}{\rho_{eff} a_{eff}^2} = \frac{1}{\rho_{mix} a_{mix}^2} + \sigma_{conduit} \quad (Eq.\ 2)$$

The cross sectional area compliance is a measure of the increase in cross-sectional area of a conduit for a given increase in internal pressure as set forth in the following relationship:

$$\sigma_{conduit} = \frac{\partial A_{crosssection}}{\partial P} \quad (Eq.\ 3)$$

For a vacuum-backed, circular cross-section conduit of elastic modulus E, having an outside radius R, and wall thickness t, the conduit compliance is given by:

$$\sigma_{conduit} = \frac{2R}{Et} \quad (Eq.\ 4)$$

It is important to note that, in general, the cross sectional area compliance of the fluid/pipe system can be a complex function of frequency and amplitude and can depend on all elements acoustically coupled to the conduit. For example, if an additional fluid surrounded the conduit, the acoustic properties of the surrounding fluid would influence the cross sectional area compliance presented to the compressional waves propagating internal to the conduit. It is for this reason that the present invention is presented in embodiments having a vacuum backed shell surrounding the sound speed meters as described above.

In accordance with the present invention, using the relationships described above, the dependence of propagation speed of compression disturbances (one dimensional, planar compression acoustic waves) on the compliance of the conduit 12 and fluid properties can be used to determine information regarding the fluid contained within the conduit 12, specifically, the density of the fluid and its phase fractions.

Referring again to FIG. 1, there is shown a density meter 1 in which the sound speed of an unknown fluid 13 is measured within two regions $X_1$, $X_2$, and in which the conduit 12 has differing cross sectional area compliances associated with the two regions. A first effective sound speed $\alpha_{eff1}$ of the fluid/pipe system is determined from an array of pressure measurements provided by sensors of sound speed meter 14. A second sound speed $\alpha_{eff2}$ of the fluid/pipe system is determined from an array of pressure measurements provided by sensors of sound speed meter 16. As will be more fully described below, the change in propagation velocity of one dimensional acoustic waves between the two regions $X_1$, $X_2$, along with knowledge of the cross sectional compliances of each section, provides a means to determine the density of the fluid 13. As illustrated in this example, the variation in the cross sectional compliance could be achieved through a change in the conduit compliance, e.g., through a change in wall thickness of the conduit. Other methods to vary the cross sectional area compliance are described below, and any known method of varying the cross sectional area compliance is contemplated by the present invention.

Figure 3:
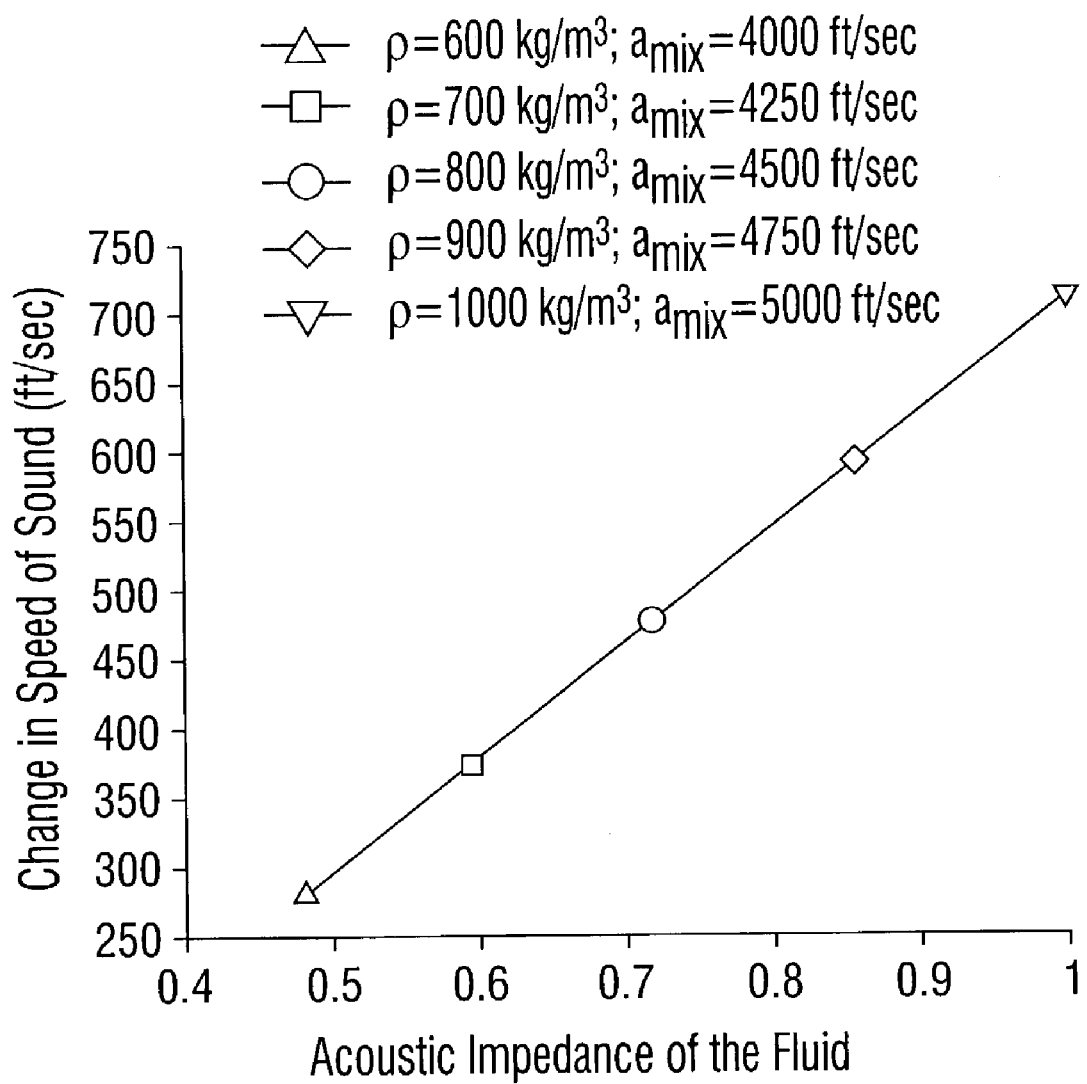
FIG. 3 is a graphical representation of the change in effective sound speed of a fluid/pipe for various fluid compliances, in accordance with the present invention.

The invention will now be described with attention to another specific embodiment commonly found in the oil and gas industry with reference to FIGS. 1 and 3, wherein varying the fluid compliance varies the cross sectional area compliance. In this exemplary embodiment, the conduit 12 is comprised of a single material type, Inconel for example, have a wall thickness $t_1$ at region $X_1$ of 0.10 inches and a wall thickness of $t_2$ at region $X_2$ of 0.35 inches. The conduit is vacuum-backed with a shell 15 that isolates the sound speed meters from the outside environment. As best shown in FIG. 3, the change in sound speed for fluid mixtures, such as representative hydrocarbon and water mixtures having densities ranging from 600 to 1000 kg/m$^3$, is quite dramatic. As shown, the change in sound speed scales with the acoustic impedance of the fluid. For the least dense fluid with the slowest infinite medium sound speed (representing a light hydrocarbon), the change in wall thickness results in approximately 300 ft/sec change in sound speed. For the densest, highest infinite medium sound speed (representing, for example, a high watercut mixture), the change in wall thickness results in a 750 ft/sec change in sound speed. The expression for the change in effective sound speed between two sections of a vacuum-backed conduit differing only in wall thickness, where $\alpha_o$ is the sound speed of the fluid and $\rho_o$ is the density of the fluid is given by:

$$a_{eff_1} - a_{eff_2} = \frac{1}{\sqrt{\frac{1}{a_0^2} + \rho_o \frac{2R}{Et_1}}} - \frac{1}{\sqrt{\frac{1}{a_0^2} + \rho_o \frac{2R}{Et_2}}} \quad (Eq.\ 5)$$

Thus in accordance with the present invention, the density of the unknown fluid is determined by measuring two effective sound speeds in two regions with differing, but known structural properties. For example, in the cylindrical conduit 12 of FIG. 1, having a thickness $t_1$ and $t_2$ and elastic modulus E, the density $\rho_{mix}$ of the unknown fluid is given by:

$$\rho_{mix} = \left( \frac{1}{a_{\it{eff1}}^2} - \frac{1}{a_{\it{eff2}}^2} \right) \frac{E}{2R} \frac{t_1 t_2}{t_2 - t_1} \quad \text{(Eq. 6)}$$

As noted above, varying wall thickness is but one way to achieve a change in cross sectional area compliance, and accordingly to measure fluid density in accordance with the present invention. In general, the larger the change in cross sectional area compliance between the two (or more regions) in which the sound speed is measured, the more robust the density measurement. In addition, an increase in the number of regions, i.e. greater than two, along a conduit with varying compliance in which sound speeds are measured would give additional, redundant measurements of density. The additional data could yield a more robust or accurate overall system depending on the specific application.

Figure 4A:
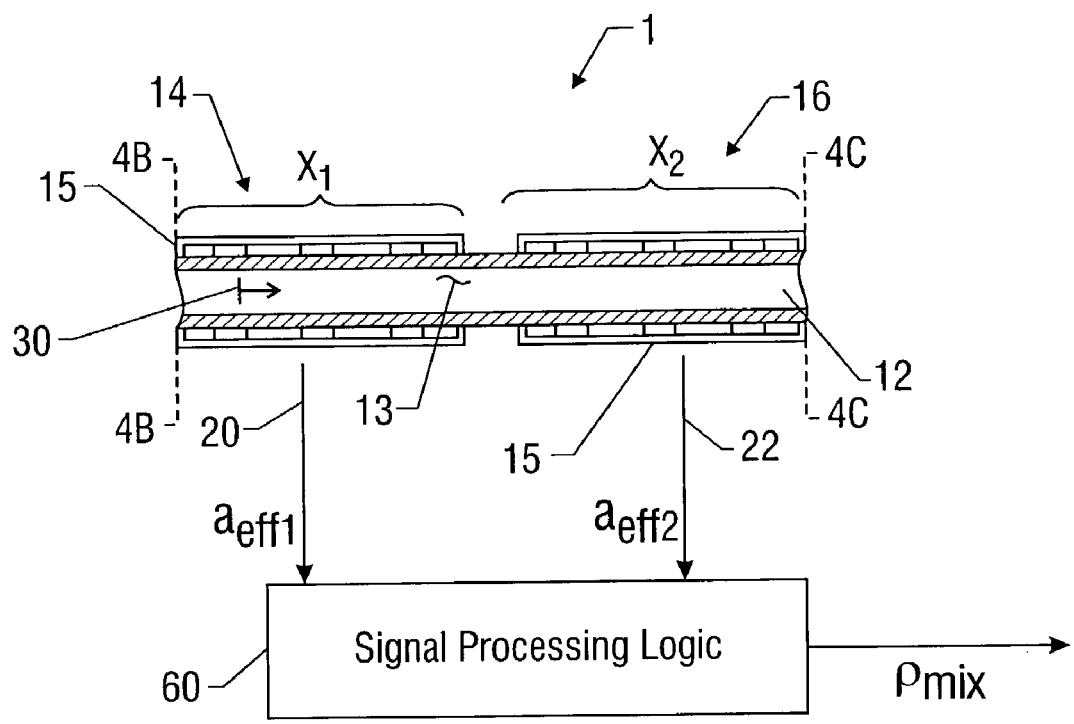
FIG. 4 is a schematic block diagram of a density meter having an egg shaped cross section in one sensing region, in accordance with the present invention.
Figure 4B:
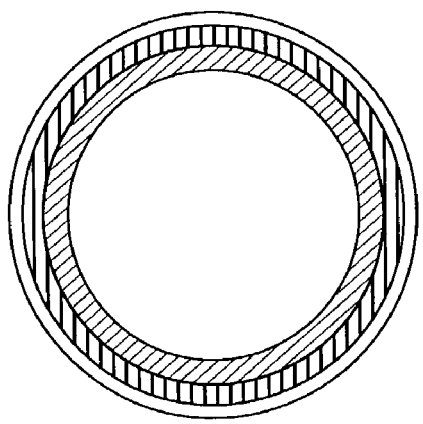
Figure 4C:
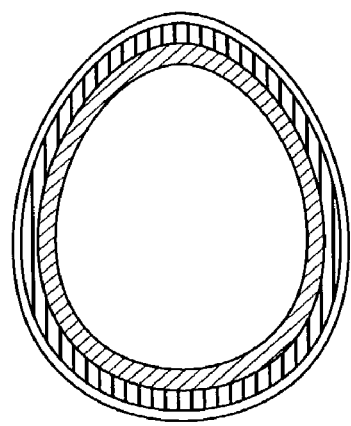

One alternative method to achieve large variations in conduit compliance is best shown with reference to FIG. 4A where a first sensing region $X_1$ comprises a circular cross sectional conduit, FIG. 4B, while a second sensing region $X_2$ comprises a non-circular cross sectional conduit, FIG. 4C (shown as an egg-shaped conduit by way of example). All other properties of the conduit, such as thickness, remain equal. The circular geometry at $X_1$ represents, for a given cross section, material modulus, and wall thickness, the configuration with the lowest cross sectional area compliance. However, the geometry of the cross section of the modified sensing region at $X_2$, formed by modifying or "egging" the circular section into an oval (or other alternative shapes such as using a cross section possessing flattened sides), significantly increases the compliance of the conduit 12. In certain embodiments between sensing region $X_2$ (non-circular geometry) and sensing region $X_1$ (circular geometry) of the same wall thickness t, cross sectional area compliance ratios greater than 30 are achievable. As demonstrated in the figures referenced above, increasing the compliance ratio of the conduit increases the sensitivity of the density meter 1 by increasing the compliance ratio, which increases the change in effective sound speed for a given fluid density.

Figure 5:
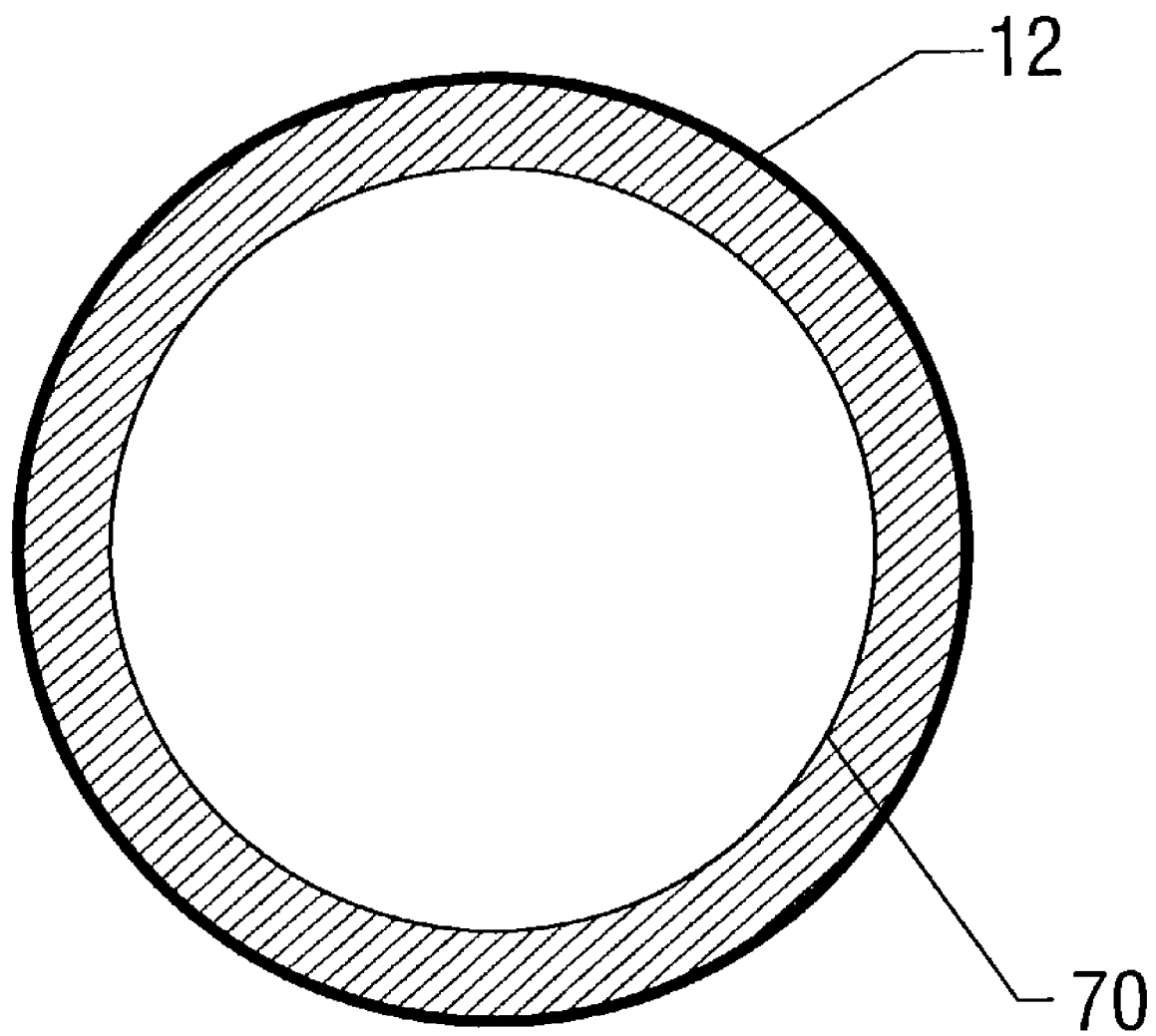
FIG. 5 is a cross sectional representation of an embodiment of a density meter having a closed cell foam liner, in accordance with the present invention.

The effective cross sectional area compliance can be modified in a variety of manners such as, by way of example, by varying materials, by incorporating wall treatments, or by incorporating resonators or cavities. Referring to FIG. 5, there is shown a modified cross sectional area compliance technique wherein a closed cell foam 70 (or other compressible liner material) is positioned along the walls of one of the sensing sections of the conduit 12 to modify the effective compliance of that section of conduit. In the embodiment shown in FIG. 5, the conduit/fluid interface would be defined as the inner surface of the liner. An increase in fluid pressure increases the effective cross sectional area of the fluid by both compressing the foam and by expanding the conduit. It is also contemplated by the present invention that the two sensing regions may be comprised of different material types or any other variation in geometry or material property that would effectuate a difference in the compliance of the conduit between the two sensing regions.

Figure 6:
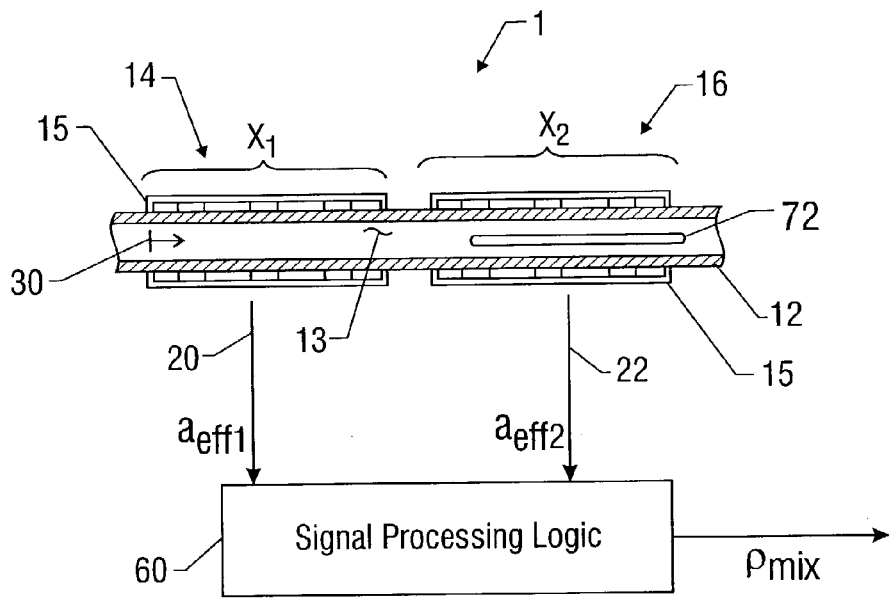
FIG. 6 is a schematic block diagram of a density meter having a tube positioned within the flow path, in accordance with the present invention.

In another example of the present invention, varying the compliance of the fluid or the area within the conduit can vary the cross sectional area compliance. For instance, and referring to FIG. 6, additional compliance could be introduced at a location along the conduit by positioning a tube 72 within the flow path along one of the sensing regions. The tube 72 would serve to modify the cross sectional compliance by compression caused by an increase in fluid pressure, which would then combine with the compliance of the conduit to modify the effective sound speed of the fluid/conduit system. Other alternatives include embodiments wherein the tube is an air filled, sealed tube (or tubes) positioned within one sensing region of the conduit.

Referring again to FIG. 1, and defining $\alpha$ as the ratio of conduit compliance in the "soft" section ($X_1$) to the "stiff" section ($X_2$) and where $\sigma_2$ is the cross sectional area compliance of sensing region $X_2$, the density of the fluid $\rho_{mix}$ within the meter can be expressed as:

$$\rho_{mix} = \frac{1}{(\alpha - 1)\sigma_2} \left( \frac{1}{a_{\it{eff1}}^2} - \frac{1}{a_{\it{eff2}}^2} \right) \quad \text{(Eq. 7)}$$

The density measurement can be used in a variety of manners to provide insight into mixture composition. For example, in a production environment, knowledge of the phase fraction of the fluid is useful in making determinations regarding the longevity and productivity of the well. When the fluid comprises substantially oil and water, the mixture density is related to the phase fractions by the following equation:

$$\rho_{mix} = \phi_{oil} \rho_{oil} + \phi_{water} \rho_{water} \quad \text{(Eq. 8)}$$

Therefore, by inserting $\rho_{mix}$ as calculated above, with known densities of oil and water and knowing that the sum of the phase fractions equals one, the equation can be solved for the individual phase fractions.

Figure 7:
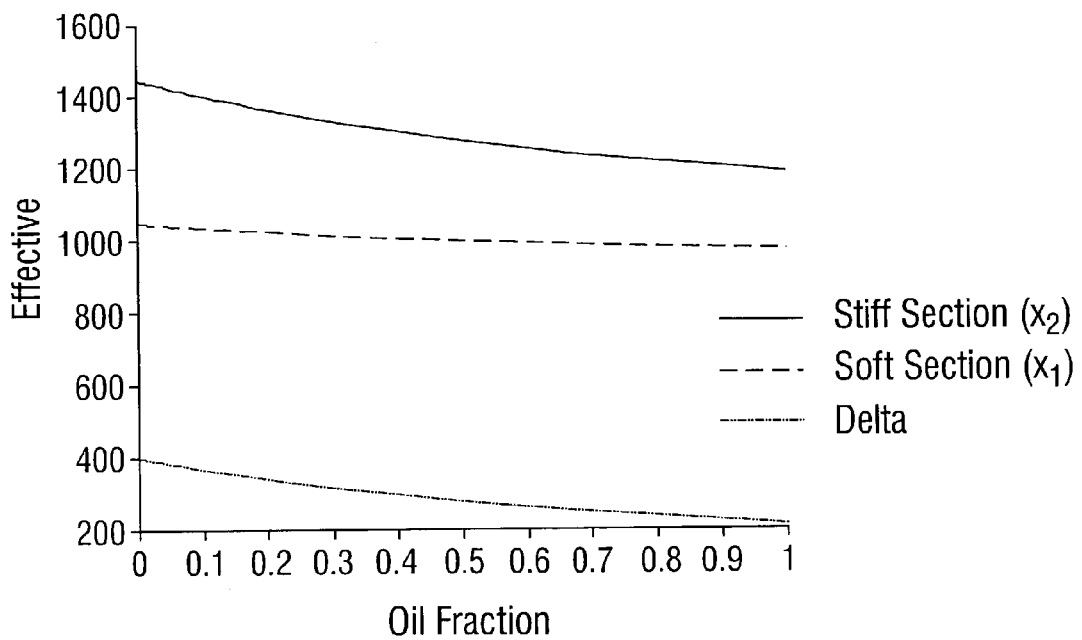
FIG. 7 is a graphical representation of the effective sound speed of a fluid/pipe for various volume fractions of a water/oil mixture, in accordance with the present invention.

Referring now to FIG. 7, there is shown the sound speed of a varying mixture as measured in two sensing regions $X_1$, $X_2$, of an embodiment of density meter 1 of FIG. 1. The figure shows the various effective sound speeds for oil/water mixtures varying from 0% oil to 100% oil by volume. In the example shown, the two sensing sections have a compliance ratio $\alpha$ of 10. As shown in FIG. 7, the difference in measured sound speed between the two sections varies from approximately 400 m/s for 100% water, to approximately 200 m/s for 100% oil. As described and depicted in the figure, the effective sound speed as measured in the stiff section ($X_2$) is significantly higher for the mixture than that measured in the soft section ($X_1$) of the conduit 12.

In operation and referring again to FIG. 1, the two sound speed meters 14, 16 provide effective sound speeds $\alpha_{eff1}$ and $\alpha_{eff2}$ to signal processing logic 60, which includes the relationship set forth in equation 7. The compliance of the conduit $\sigma_2$ in the second sensing region $X_2$ and the ratio of the compliances between the two sections $\sigma_1/\sigma_2$ are further provided to logic 60 to calculate the density of the mixture, $\rho_{mix}$. Thus the density of the fluid mixture can be determined without requiring specific sound speed and calibration information concerning the fluid itself. In the embodiments described thus far, it is only required that the infinite sound speed ($\alpha_{mix}$) and density of the fluid itself is the same in the two sections. Thus, although the density measurement described is based on sound speed measurements, no knowledge of the infinite sound speed ($\alpha_{mix}$) of the fluid is required to determine density.

Figure 8:
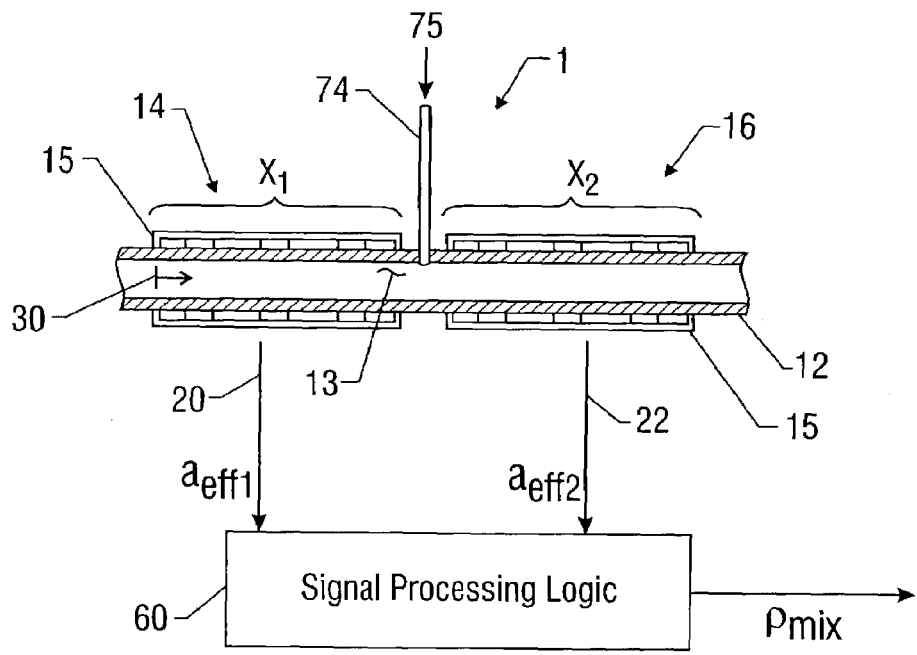
FIG. 8 is a schematic block diagram of a density meter having an input tube positioned between the sensing regions, in accordance with the present invention.

In certain other embodiments, the density of the fluid may be determined after the introduction of a known quantity of a known constituent into the fluid between the two sensing sections. Referring to FIG. 8, there is shown a density meter 1 including an input line 74 positioned between the two sensing sections $X_1$, $X_2$. In this particular embodiment, the cross sectional area compliance is changed by the introduction of a constant amount of a known quantity of air 75, for example, into the fluid 13. The introduction of the air into the fluid changes the cross-sectional area compliance in the sensing region ($X_2$) downstream of input line 74. The change in compliance in the fluid due to the introduction of the air is taken into account in the relationships described above to accurately determine the density of the fluid 13.

Figure 9:
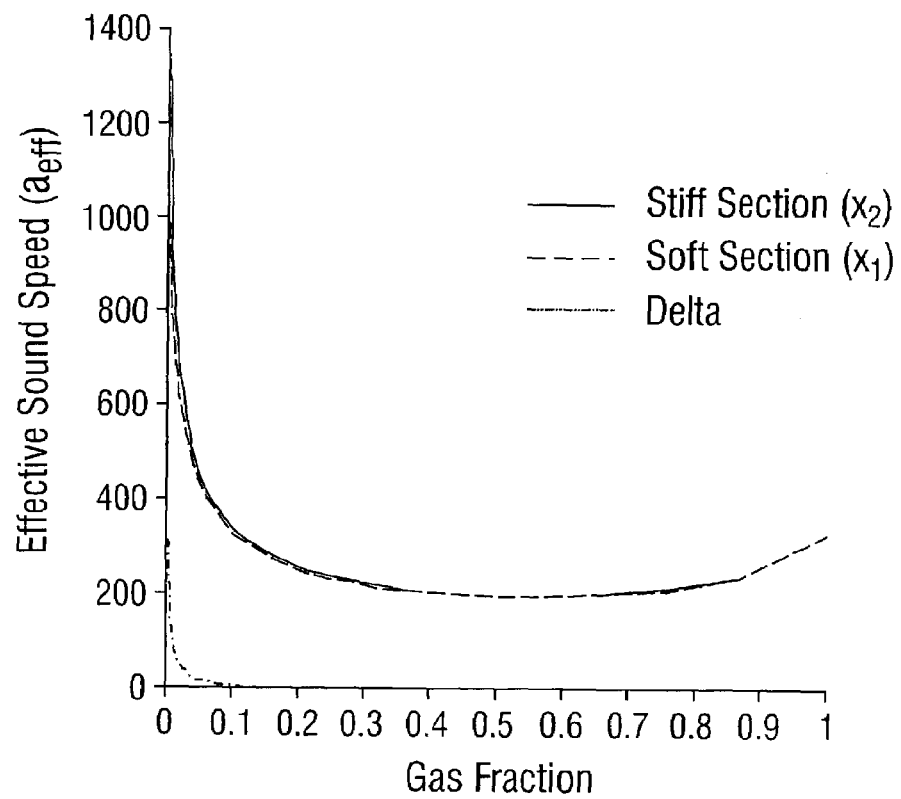
FIG. 9 is a graphical representation of the effective sound speed of a fluid/pipe for various volume fractions of a gas/fluid mixture, in accordance with the present invention.

In addition to liquid mixtures, the density meter of the present invention includes the ability to determine the density of gas/liquid mixtures. Referring to FIG. 9, there is shown the predicted sound speeds in the stiff ($X_2$) and soft ($X_1$) sensing regions of density meter 1 of FIG. 1 for various mixtures of gas and liquids with representative single phase compliances typical of produced gases and liquids at 100 bar. As shown, due primarily to the high compliance of the gas phase at this relatively low pressure, the change in overall sound speed in the two sections of the meter due to the change in conduit compliance is much less significant for this application than those described above. Using Equation 2, and by defining the compliance of the fluid as the inverse of the product of the fluid density and the square of the infinite dimensional sound speed, the following relation results:

$$\sigma_{mixture} \equiv \frac{1}{\rho_{mix} a_{mix}^2} \qquad \text{(Eq. 9)}$$

and the ratio of the effective sound speed within the conduit to the infinite dimensional sound speed is given by:

$$\frac{a_{eff}}{a_{mix}} = \sqrt{\frac{1}{1 + \frac{\sigma_{conduit}}{\sigma_{mixture}}}} \qquad \text{(Eq. 10)}$$

The change in difference in sound speed for a given change in density of the fluid is a useful metric in designing the density meter described for any specific application. Assuming that the ratio of the cross sectional compliance introduced by the structure over that of the fluid is much less than 1, this performance metric can be expressed as follows:

$$\frac{\partial(a_{1_{eff}} - a_{2_{eff}})}{\partial \rho} = \frac{a_{mix}}{\rho_{mix}} \frac{\sigma_{Stiff}}{\sigma_{mixture}} \frac{1}{2}(\alpha - 1) \qquad \text{(Eq. 11)}$$

As shown, effectiveness of the density meter of the present invention described scales with both the ratio of the compliances of the two conduits as well as with the ratio of the compliance of the conduit to that of the fluid. Thus, the density meter of the present invention is more effective when the cross sectional area compliance contributed by the conduit is a significant fraction of that contributed by the fluid and the ratio of the cross sectional area compliance of the two regions is significantly greater than one. Therefore as one skill in the art would realize, with an increasing gas fraction of the fluid, the compliance of the fluid would also increase, and thus the relationship between fluid sound speed and phase fraction degrades. Experience has found that there may be performance limitations for flows above 20% gas volume fraction, but for low gas volume fractions the invention disclosed uniquely determines the phase fractions of not only a two phase mixture, but also a three phase mixture.

The phase fraction for a three-phase fluid is determined in the basic manner described. By using acoustic signal processing techniques such as disclosed in incorporated reference '147, the infinite fluid sound speed $\alpha_{mix}$ can be determined. By combining the infinite fluid sound speed $\alpha_{mix}$ from one of the sensing regions, or from a separate acoustic sensor array, with the difference in effective sound speeds, the device described is capable of measuring the phase fractions of a three-phase mixture, e.g., of gas, oil, and water. The sound speed in a fluid is related to the phase fraction of the fluid and the densities of the components of the fluid by the equations:

$$\frac{1}{\rho_{mix} a_{mix}^2} = \sum_{i=1}^{N} \frac{\phi_i}{\rho_i a_i^2}; \rho_{mix} = \sum_{i=1}^{N} \phi_i \rho_i; \sum_{i=1}^{N} \phi_i = 1 \qquad \text{(Eq. 12)}$$

where $\rho_{mix}$ is the density of the fluid, $\rho_i$ is the density of the $i^{th}$ component, $\alpha_{mix}$ is the sound speed in the fluid, $\alpha_i$ is the sound speed of the $i^{th}$ component, $\phi_i$ is the phase fraction of the $i^{th}$ component, and N is the number of phases in the fluid, in this case three. The density $\rho_i$ and sound speed $\alpha_i$ for each of the individual components can be known or measured independently. The density meter as described above measures/calculates and the density of the fluid $\rho_{mix}$, i.e., using the differences in the cross sectional compliances of the pipe/fluid system, and the sound speed in the fluid $\alpha_{mix}$ can be determined as disclosed in the '147 patent, possibly using one or both of the same meters 14, 16 used in the density meter. Therefore, for a fluid consisting of three components, the equations above yield a system of three equations and three unknowns, the unknowns being phase fractions $\phi_1$, $\phi_2$, and $\phi_3$. The equations are therefore easily solvable for the phase fractions of each of the components. Such calculations, and interpretation of the signals coming from the meters 14, 16 are easily performed by signal processing logic 60 as one skilled in the art will appreciate.

It should be understood that any of the features, characteristics, alternatives or modifications described regarding a particular embodiment may also be applied, used, or incorporated with any other embodiment described.

While two discrete sound speed meters 14, 16 have been disclosed, it should be noted that the sound speed meters can comprise an integrated singular meter spanning two sections along the pipe having different cross sectional compliancies as disclosed herein. This alternative embodiment is facilitated by the use of fiber optic based meters, such as those incorporated herein. As explained in the incorporated references, in a fiber based meter, the speed of sound meters 14, 16 can comprise an array comprising a series of wraps separated by fiber Bragg gratings, with each of the wraps providing a pressure signal which can be interpreted by the signal processor to determine sound speed. In this regard, some of the wraps (at least one wrap) of fiber optic based flow meters, e.g., those wrapped around a pipe section of a first compliance, can be said to constitute a first meter, while the other wraps (at least one wrap), e.g., those wrapped around a pipe section of a second compliance, can be said to constitute a second meter, even though the fiber optic based meter is integrated. Optionally, fiber optic based meters allow two discrete speed of sound meters to be multiplexed along a single fiber optic cable, e.g., using wavelength division multiplexing or time division multiplexing, as is known.

Although the invention has been described and illustrated with respect to exemplary embodiments thereof, the foregoing and various other additions and omissions may be made therein and thereto without departing from the spirit and scope of the present invention.

What is claimed is:

1. An apparatus for determining the phase fractions of a fluid mixture in a pipe, comprising:
    a first speed of sound meter coupled to the outside of a first section of the pipe for determining a first effective speed of sound in the fluid mixture, wherein the first pipe section has a first compliancy;
    a second speed of sound meter coupled to the outside of a second section of the pipe for determining a second effective speed of sound in the fluid mixture, wherein the second pipe section has a second compliancy different from the first compliancy; and
    a signal processor for receiving the first and second effective speeds of sound to determine the phase fractions of the fluid mixture based on a calculation that includes the first and second effective speeds of sound.

2. The apparatus of claim 1, wherein the fluid mixture is flowing in the pipe.

3. The apparatus of claim 1, wherein the fluid mixture comprises components selected from the group consisting of gas, water, and oil.

4. The apparatus of claim 1 wherein either or both of the first and second speed of sound meters are comprised of fiber optic cable.

5. The apparatus of claim 4, wherein the fiber optic cable comprises at least one winding around an outer surface of the pipe.

6. The apparatus of claim 4, wherein the fiber optic cable comprises an array of windings around an outer surface of the pipe.

7. The apparatus of claim 6, wherein the windings are separated by fiber Bragg gratings.

8. The apparatus of claim 1, wherein the first and second pipe sections are of different thicknesses.

9. The apparatus of claim 1, wherein the first and second pipe sections are of different cross-sectional geometries.

10. The apparatus of claim 1, wherein the first and second pipe sections are comprised of different materials.

11. The apparatus of claim 1, further comprising a housing coupled to an outside surface of the pipe to protect the first and second speed of sound meters.

12. The apparatus of claim 1, wherein the signal processor determines the density of the fluid mixture by comparing the first and second effective speeds of sound.

13. The apparatus of claim 1, wherein either the first or second speed of sound meters further determines an Infinite speed of sound in the fluid mixture, and wherein the signal processor also receives the infinite speed of sound to determine the phase fractions of the fluid mixture.

14. The apparatus of claim 1, further comprising a third speed of sound meter coupled to the outside of a third section of the pipe for determining an infinite speed of sound in the fluid mixture, and wherein the signal processor also receives the infinite speed of sound to determine the phase fractions of the fluid mixture.

15. An apparatus for determining the phase fractions of a fluid mixture in a pipe, comprising:
    a meter coupled to the outside of the pipe for measuring first and second effective speeds of sound in the fluid mixture, wherein the first and second effective speeds of sound are different; and
    a signal processor for receiving the first and second effective speeds of sound to determine the density of the fluid mixture based on a calculation that includes the first and second effective speeds of sound, wherein the signal processor also determines the phase fractions of the fluid mixture using the density.

16. The apparatus of claim 15, wherein the fluid mixture is flowing in the pipe.

17. The apparatus of claim 15, wherein the fluid mixture comprises components selected from the group consisting of gas, water, and oil.

18. The apparatus of claim 15, wherein the meter is comprised of fiber optic cable.

19. The apparatus of claim 18, wherein the fiber optic cable comprises at least one winding around an outer surface of the pipe.

20. The apparatus of claim 18, wherein the fiber optic cable comprises an array of windings around an outer surface of the pipe.

21. The apparatus of claim 20, wherein the windings are separated by fiber Bragg gratings.

22. The apparatus of claim 15, wherein the meter comprises a first meter at a first section of the pipe and a second meter at a second section of the pipe.

23. The apparatus of claim 22, wherein the first and second pipe sections are of different thicknesses.

24. The apparatus of claim 22, wherein the first and second pipe sections are of different cross-sectional geometries.

25. The apparatus of claim 22, wherein the first and second pipe sections are comprised of different materials.

26. The apparatus of claim 15, further comprising a housing coupled to an outside surface of the pipe to protect the meter.

27. The apparatus of claim 15, wherein the meter further determines an infinite speed of sound in the fluid mixture, and wherein the signal processor also receives the infinite speed of sound to determine the phase fractions of the fluid mixture.

28. The apparatus of claim 15, further comprising a speed of sound meter coupled to the outside of the pipe for determining an infinite speed of sound in the fluid mixture, and wherein the signal processor also receives the infinite speed of sound to determine the phase fractions of the fluid mixture.

29. A method for determining the phase fractions of a fluid mixture in a pipe, comprising:
    measuring a first effective speed of sound in the fluid mixture at a first pipe section having a first compliancy to produce at least one first signal indicative of the first effective speed of sound;
    measuring a second effective speed of sound in the fluid mixture at a second pipe section having a second compliancy different from the first compliancy to produce at least one second signal indicative of the second effective speed of sound; and processing at least the first and second signals to determine the phase fractions of the fluid mixture.

30. The method of claim 29, further comprising flowing the fluid mixture in the pipe.

31. The method of claim 29, wherein the fluid mixture comprises components selected from the group consisting of gas, water, and oil.

32. The method of claim 29, wherein measuring either or both of the first or second effective speeds of sound comprises the use of a fiber optic cable.

33. The method of claim 32, wherein the fiber optic cable comprises at least one winding around an outer surface of the pipe.

34. The method of claim 32, wherein the fiber optic cable comprises an array of windings around an outer surface of the pipe.

35. The method of claim 34, wherein the windings are separated by fiber Bragg gratings.

36. The method of claim 29, wherein the first and second pipe sections are of different thicknesses.

37. The method of claim 29, wherein the first and second pipe sections are of different cross-sectional geometries.

38. The method of claim 29, wherein the first and second pipe sections are comprised of different materials.

39. The method of claim 29, wherein the processing determines the density of the fluid mixture by comparing the first and second effective speeds of sound.

40. The method of claim 29, further comprising measuring an infinite speed of sound in the fluid mixture to produce at least one third signal indicative of the infinite speed of sound, and wherein the processing also receives the third signal to determine the phase fractions of the fluid mixture.

41. The method of claim 40, wherein the third signal is produced by a meter not used to produce the first or second signals.

* * * * *